(12) United States Patent
Davies

(10) Patent No.: US 8,536,139 B2
(45) Date of Patent: Sep. 17, 2013

(54) COMPOSITIONS COMPRISING LIPOTEICHOIC ACID FOR USE IN TREATING PLEURAL EFFUSION OR PNEUMOTHORAX

(75) Inventor: Robert John Oriel Davies, Oxfordshire (GB)

(73) Assignee: ISIS Innovation Limited, Oxfordshire (GB)

( * ) Notice: Subject to any disclaimer, the term of this patent is extended or adjusted under 35 U.S.C. 154(b) by 513 days.

(21) Appl. No.: 12/676,742

(22) PCT Filed: Sep. 8, 2008

(86) PCT No.: PCT/GB2008/003019
§ 371 (c)(1),
(2), (4) Date: Sep. 10, 2010

(87) PCT Pub. No.: WO2009/030929
PCT Pub. Date: Mar. 12, 2009

(65) Prior Publication Data
US 2011/0059908 A1 Mar. 10, 2011

(30) Foreign Application Priority Data
Sep. 7, 2007 (GB) .................................. 0717442.8

(51) Int. Cl.
*A01N 43/04* (2006.01)
*A61K 31/70* (2006.01)

(52) U.S. Cl.
USPC ........................................................ 514/25

(58) Field of Classification Search
USPC ........................................................ 514/25
See application file for complete search history.

(56) References Cited

FOREIGN PATENT DOCUMENTS

| WO | WO 96/23896 A | 8/1996 |
|---|---|---|
| WO | WO 2005/030133 A | 4/2005 |
| WO | WO 2008/048560 A | 4/2008 |

OTHER PUBLICATIONS

Sahn, Steven, Monaldi Arch Chest Dis, 2001, 56, 394-399.*
Kovak et al., the English abstract of Journal of the American Veterinary Medical Association, 2002, 221, p. 990, retrieved from Internet <http://avmajournals.avma.org/doi/abs/10.2460/javma.2002.221.990> on Jan. 15, 2013, 2 page.*
Muraoka et al., Journal of Surgical Oncology, 2006, 93, 323-329.*
Seto et al., British Journal of Cancer., 2006, 95, 717-721.*
Colt, H. G. et al., "The ideal pleurodesis agent:still searching after all these years" The Lancet Oncology (Oct. 2008) 9(10):912-913.
Ginsburg, I., "Role of lipoteichoic acid in infection and inflammation" The Lancet Infectious Disease (Mar. 2002) 2(3):171-179.
Hasse et al.,Lung, Abstracts 46-55, Posters, Pathology Research and Practice (Jan. 2003) 199(4):190-193.
Imamura, F. "Phase II Study of whole peptidoglycan (WPG) . . . effusion", Lung Cancer Elsevier Amsterdam NL (Jan. 1991)7: 113 Abstract.
Rahman, N. et al., "Use of lipoteichoic acid-T for pleurodesis in malignant . . . study" The Lancet Oncology (Oct. 2008) 9(10):946-952.
Tschopp, J-M et al., "Talcage by medical thoracoscopy . . . study", Eur Respir J (2002) 20: 1003-1009.

* cited by examiner

*Primary Examiner* — Eric S Olson
*Assistant Examiner* — Zhengfu Wang
(74) *Attorney, Agent, or Firm* — Karen S. Canady; Canady + Lortz LLP

(57) ABSTRACT

The present invention relates to lipoteichoic acid T for use in treating pleural effusion or pneumothorax. The present invention also relates to the use of lipoteichoic acid T (LTA-T) in the manufacture of a medicament for treating pleural effusion or pneumothorax. The present invention also relates to a kit comprising a pharmaceutical composition comprising lipoteichoic acid T and instructions indicating that the composition is for use as a pleurodesis agent. In addition, the present invention relates to a method of treating pleural effusion or pneumothorax comprising administration of lipoteichoic acid T to a subject.

20 Claims, 4 Drawing Sheets

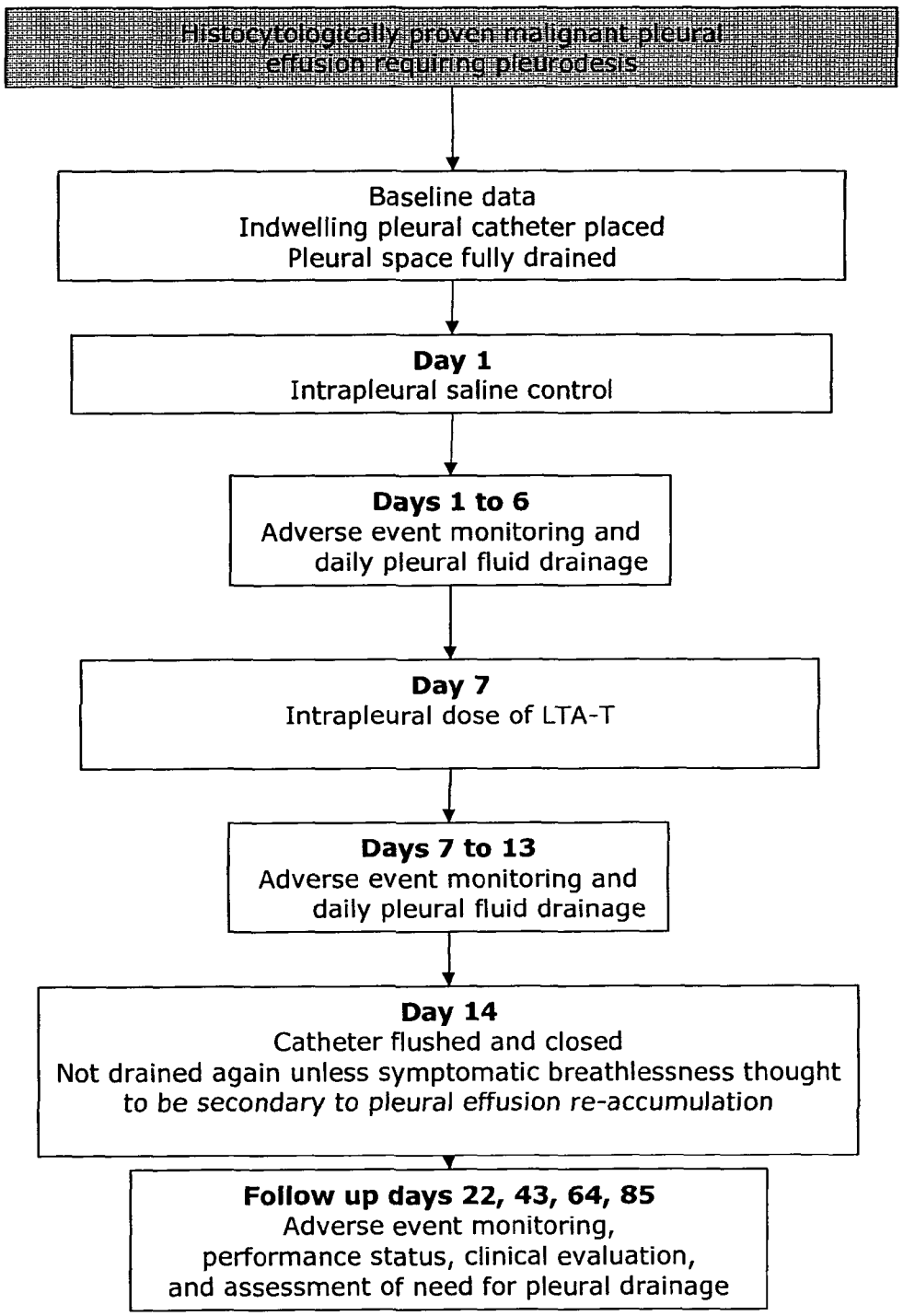
Figure 1. Chronological scheme of trial

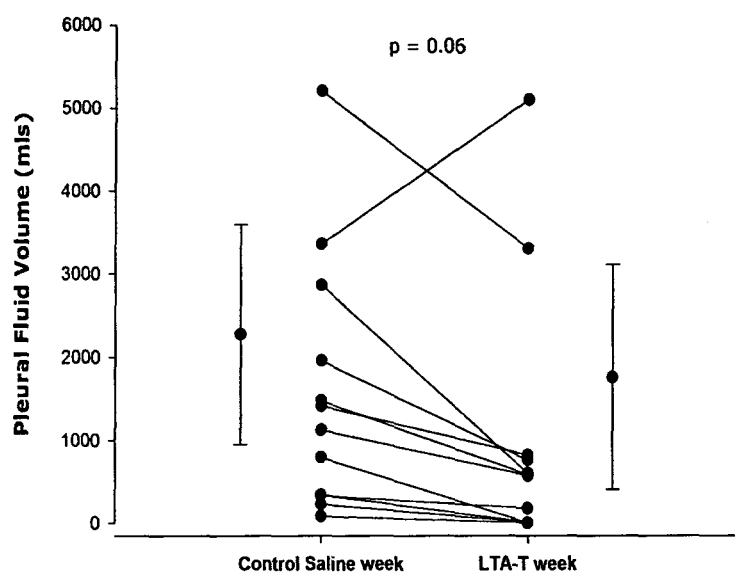
Figure 2a. Pleural fluid production by week of study in all patients. Individual patient results are shown in addition to mean and error bars for each group. P value derived from paired t-test

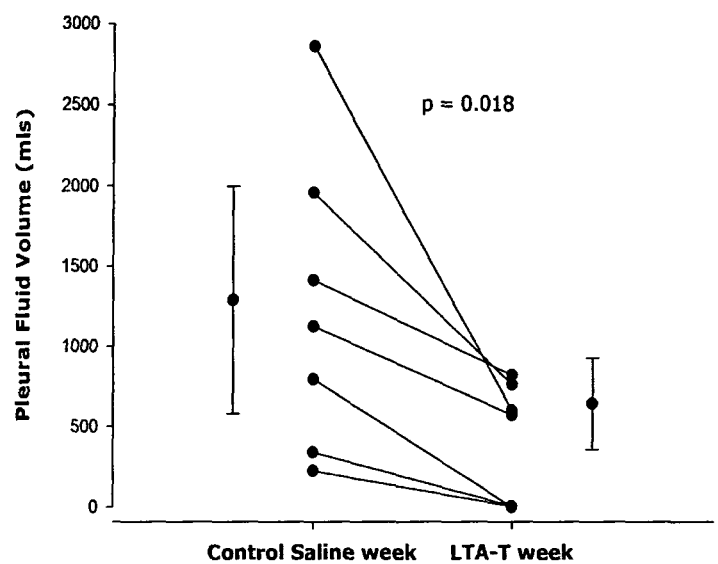
Figure 2b. Pleural fluid production by week of study in patients recieving 750mcg LTA-T or more. Individual patient results are shown in addition to mean and error bars for each group. P value derived from paired t-test

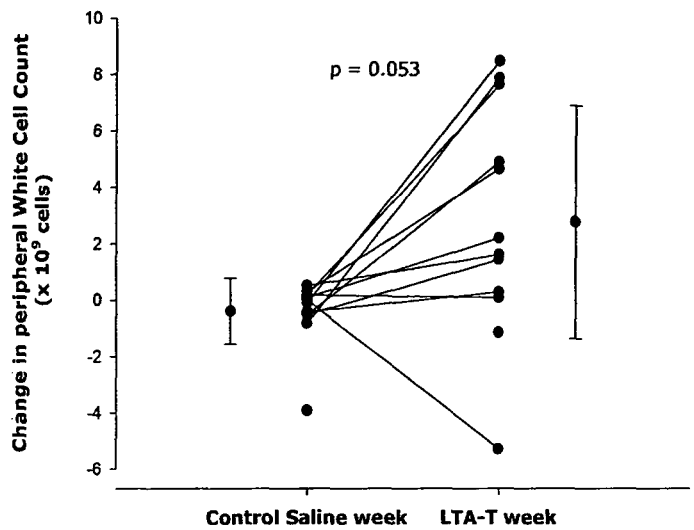

Figure 3a. Change in peripheral white cell count 24 hours after administration of intrapleural saline control or LTA-T, in all patients. Individual results are shown and mean and SD data for each group.

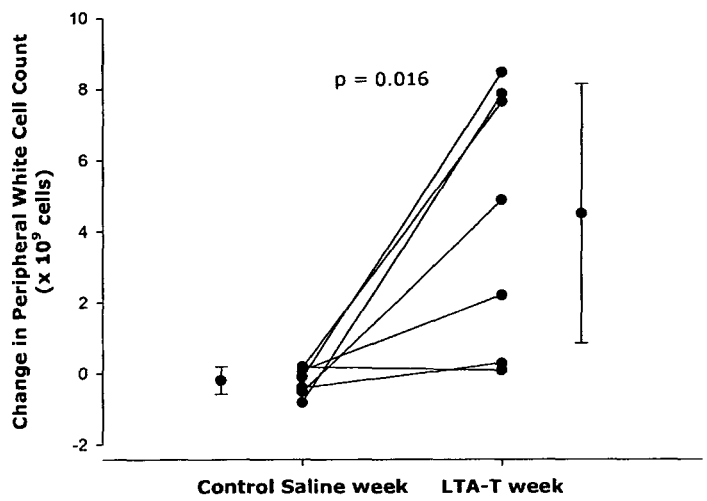

Figure 3b. Change in peripheral white cell count 24 hours after administration of intrapleural saline control or LTA-T, in patients recieving 750mcg LTA-T or more. Individual results are shown and mean and SD data for each group.

COMPOSITIONS COMPRISING LIPOTEICHOIC ACID FOR USE IN TREATING PLEURAL EFFUSION OR PNEUMOTHORAX

The present invention relates to lipoteichoic acid T for use in treating pleural effusion or pneumothorax. The present invention also relates to the use of lipoteichoic acid T (LTA-T) in the manufacture of a medicament for treating pleural effusion or pneumothorax. The present invention also relates to a kit comprising a pharmaceutical composition comprising lipoteichoic acid T and instructions indicating that the composition is for use as a pleurodesis agent. In addition, the present invention relates to a method of treating pleural effusion or pneumothorax comprising administration of lipoteichoic acid T to a subject.

Each year, over half a million patients in westernised countries require adherence of their parietal and visceral pleural membranes, adhering the lung to the chest wall (pleurodesis) to control unwanted collections of fluid or air in the pleural space (the space between the lung and the chest wall), induced by a number of diseases.

Therapeutic drainage is effective in treating breathlessness caused by pleural fluid but the majority of effusions recur after single drainage (Antunes G et al., *Thorax* 2003; 58 Suppl 2: ii 29-ii 38) and require painful repeated drainage or adherence of the lung to the chest wall by pleurodesis that requires about a week in hospital. Currently there are no licensed intrapleural treatments for pleural effusion or pneumothorax.

The agents that are currently used to treat pleural effusion or pneumothorax are not licensed for these indications. The most commonly used agent is sterilised medical grade talcum (talc) powder. This is only partially effective (causing effective pleurodesis in only about 70% of patients with pleural effusion in the long-term and about 90% of patients with pneumothorax), is very painful when used (Tschopp J M et al., *Eur Respir J* 2002; 20(4): 1003-1009, Stefani A et al., *Eur J Cardiothorac Surg* 2006; 30(6): 827-832) and can cause severe, occasionally life-threatening, and sometimes fatal depression of the blood oxygen levels due to lung inflammation in patients receiving it (for example, Campos J R, Werebe E C, Vargas F S, Jatene F B, Light R. W. *Lancet* 1997; 394: 251-252, and Maskell N A et al., *Am J Respir Crit Care Med* 2004; 170(4): 377-382). This complication occurs in greater than 1% of patients receiving standard talc pleurodesis (Dresler C M, Olak J, Herndon J E, Richards W G, Scalzetti E, Fleishman S B et al. *Chest* 2005; 127(3): 909-915.).

Thus, there is a clear need for a new, effective pleurodesis agent having reduced side effects.

The present invention relates to the treatment of conditions where the pleural membrane has become separated from the chest wall. This includes the treatment of pleural effusion, where fluid collects in the space between the pleural membrane and the chest wall and pneumothorax, where air collects in the space between the pleural membrane and the chest wall.

The first aspect of the present invention provides lipoteichoic acid T (LTA-T) for use in treating pleural effusion or pneumothorax.

LTA-T is a gram positive pathogen cell wall motif that allows the pathogen to be immunologically recognised by binding to Toll-like receptors on the cell surface. LTA-T is strongly pro-inflammatory in animal models of sepsis, mediating its effects through the Toll-like receptor pathway (via TLR-2), which activates NF-Kβ signalling. LTA-T is described in U.S. Pat. No. 6,114,161 for use as an antitumour preparation. All aspects of LTA-T from U.S. Pat. No. 6,114,161 are incorporated herein by reference.

The present invention also includes any substance that binds TLR2, and induces inflammation, for treating pleural effusion or pneumothorax. Such substance include peptidoglycan, atypical LPS, MALP-2 and MALP-404 (lipoproteins), OspA, porin, antigen mixtures, LcrV, lipomannan, GPI anchor, lysophosphatidylserine, lipophosphoglycan (LPG), zymosan, hsp60 and hemagglutinin.

LTA-T is sensed by inflammatory cells and triggers inflammation. The present invention shows for the first time that the inflammation induced by LTA-T leads to therapeutically useful adhesion between the pleural membranes. This inflammation stimulates the production of fibrin within the pleural cavity, which is later invaded by scar tissue (collagen), adhering the pleural membranes. This adherence of the pleural membranes prevents the collection of unwanted fluid or air in the pleural cavity which causes breathlessness and other medical complications.

Pleural effusion is excess fluid that accumulates in the pleural cavity, the fluid-filled space that surrounds the lungs. Pleural effusions can be caused by a number of different diseases and conditions, such as cancer, heart failure, diseases causing low blood protein levels (for example liver cirrhosis and nephrotic syndrome), bacterial pneumonia, tuberculosis, pulmonary embolism, and diseases causing pleural inflammation (for example, systemic lupus erythematosus, rheumatoid arthritis and other autoimmune diseases), bleeding (often due to chest trauma), chylothorax, accidental infusion of fluids, oesophageal rupture or pancreatic disease, intra-abdominal abscess, rheumatoid arthritis, asbestos pleural effusion, Meig's syndrome and ovarian hyperstimulation syndrome.

Pneumothorax is air in the pleural cavity. Pneumothorax can be caused by a number of different diseases and conditions, such as a penetrating chest wound, barotrauma to the lungs, chronic lung pathologies including emphysema, asthma, acute infections, acupuncture, chronic infections, such as tuberculosis, cancer and catamenial pneumothorax (due to endometriosis in the chest cavity), and can also arise without significant underlying lung disease in the form of a primary spontaneous pneumothorax.

The LTA-T may be in the form of a pharmaceutical composition as herein described as part of this invention.

In the present invention, a subject to be treated may be suffering from one or more of these diseases/conditions or any other disease/condition where pleural effusion or pneumothorax has occurred.

In one embodiment of the invention, the LTA-T can be used in combination with a further pleurodesis agent. Administration of LTA-T and other pleurodesis agents can be simultaneously, separately and/or sequentially.

A pleurodesis agent is any agent given into the pleural space that can be used to treat pleural effusion or pneumothorax.

The other pleurodesis agent can be intrapleural talc, minocycline, *Cornebacterium parvum*, doxycycline, tetracycline, methylprednisolone acetate, fluorouracil, bleomycin, interferon-B, mitomycin-C, cisplatin, doxorubicin, TGF-beta, quinacrine, 2% polydocanol, OK-432, *Streptococcus pyogenes*, fibrin tissue adhesive, povidone iodine (Betadine), silver iodide, barium sulphate, plidocanol, etoposide or ipovidone, or any other substance administered into the pleural space to control pleural fluid or air in the pleural space.

According to the present invention, LTA-T for pleurodesis is by intra-pleural administration. Where the LTA-T is administered with another pleurodesis agent, both are preferably administered intra-pleurally.

The second aspect of the invention is a kit comprising a pharmaceutical composition comprising LTA-T and instructions indicating that the composition is for use as a pleurodesis agent. A pleurodesis agent is an agent for treating pleural effusion or pneumothorax, preferably by intra-pleural administration.

Pharmaceutical compositions in accordance with the invention may be supplied as part of a sterile, pharmaceutical composition which will normally include a pharmaceutically acceptable carrier. This pharmaceutical composition may be in any suitable form. It may be provided in unit dosage form and will generally be provided in a sealed container. The kit of the invention may comprise a plurality of said unit dosage forms.

The pharmaceutical compositions may be formulated as solutions or suspensions. For the preparation of solutions, excipients which may be used include, for example, water, polyols and sugars. For the preparation of suspensions, inert oils (e.g. vegetable oils) may be used to provide oil-in-water or water in oil suspensions.

The pharmaceutical compositions may contain preserving agents, solubilising agents, stabilising agents, wetting agents, emulsifiers, sweeteners, colourants, odourants, salts, buffers, coating agents or antioxidants. They may also contain further therapeutically active agents.

Dosages of the substances of the present invention can vary between wide limits, depending upon the condition to be treated, the health of the individual to be treated, etc. and a physician may determine appropriate dosages to be used. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of LTA-T which produces a therapeutic effect.

In one embodiment, the dosage of LTA-T according to the present invention is between 250 micrograms and 3000 micrograms including 300 micrograms to 400 micrograms, 700 micrograms to 800 micrograms and 1450 micrograms to 1550 micrograms. In a further embodiment, the dosage of LTA-T according to the present invention is between 750 micrograms to 1500 micrograms (10-20 micrograms/kilogram) including 900 micrograms to 1100 micrograms. The dosage may be repeated as often as appropriate.

In a yet further embodiment, the dosage of LTA-T is between 50 micrograms to 550 micrograms, including 100 micrograms to 250 micrograms, 250 micrograms to 400 micrograms and 400 to 550 micrograms, and is administered repeatedly. The dosage may be repeated hourly, daily, weekly or over any other appropriate time period.

The compositions and uses described in this application are envisaged to have human and veterinary applications. They are preferably applicable to mammals, in particular humans, but are also applicable for use in production animals, in particular sheep, cows, pigs, chickens and goats, as well as companion animals, in particular cats and dogs and sporting animals, such as horses.

The third aspect of the invention is a method of treating pleural effusion or pneumothorax comprising administering LTA-T to a subject. In the third aspect of the invention, the method is preferably carried out on a subject in need of treatment. In one embodiment, the subject is a mammal. In a further embodiment, the subject is a human. The LTA-T may be in the form of a pharmaceutical composition as herein described as part of this invention.

In the present invention, the term "treatment" is primarily therapeutic treatment. However, LTA-T can be administered to a pleural cavity that does not contain fluid or air after pneumothorax or pleural effusion has been resolved to stop recurrence of pneumothorax or pleural effusion.

The fourth aspect of the invention is the use of lipoteichoic acid T (LTA-T) in the manufacture of a medicament for treating pleural effusion or pneumothorax.

The preferred embodiments, as described for the first aspect of the invention, are the same for other aspects of the invention mutatis mutandis.

Unless otherwise defined, all technical and scientific terms used herein have the meaning commonly understood by a person who is skilled in the art in the field of the present invention.

The present invention is described with reference to the figures, in which:

FIG. 1 illustrates the chronological scheme of the clinical trial conducted to test LTA-T for treating pleural effusion.

FIG. 2 illustrates pleural fluid production by week of study in all patients (FIG. 2a) and patients receiving 750 mcg LTA-T or more (FIG. 2b). Individual patient results are shown in addition to mean and error bars for each group. P value derived from paired t-test.

FIG. 3 illustrates the change in peripheral white cell count 24 hours after administration of intrapleural saline control or LTA-T, in all patients (FIG. 3a) and patients receiving 750 mcg LTA-T or more (FIG. 3b). Individual results are shown and mean and SD data for each group.

The present invention is described with reference to the following non-limiting examples:

EXAMPLES

Methods

The study was a phase I/IIa toxicity/non-randomised "proof of concept" efficacy trial. The protocol included administration of an intrapleural saline control followed by seven days pleural fluid production measurement prior to the administration of LTA-T to allow the assessment of any side-effects from LTA-T administration, and both acute pleural fluid production changes and the frequency of long-term pleurodesis efficacy after intrapleural LTA-T (see FIG. 1).

The subjects were adults (aged≧18) with histocytologically proven malignant pleural effusion requiring symptomatic treatment.

After informed consent, an indwelling pleural catheter (PleurX, Denver, Colo.) was placed in the pleural effusion and the pleural space fully drained. Markers of toxicity (clinical symptoms, blood parameters, performance status) were recorded daily on the first 14 days of the study and at intervals thereafter (FIG. 1).

After initial complete fluid drainage, 30 mls intra-pleural saline (saline control) was administered (day 1). The daily pleural fluid drainage was then recorded for seven days to quantify the rate of production of pleural fluid. On day seven, subjects received a single intra-pleural injection of LTA-T, according to the dosing schedule (table 1). The starting dose was 250 mcg. Patients remained in hospital for one night following LTA-T administration in a respiratory unit equipped for the care of acute respiratory failure to permit immediate adverse event monitoring.

Over the next 7 days (days 7-14), daily pleural fluid volume drainage and pleural fluid cytology for malignant cells was performed unless pleural fluid flow ceased. On day 14, the intra-pleural catheter was flushed and closed (but left in situ) and not used again for the duration of the study unless recurrent pleural fluid caused breathlessness requiring treatment by fluid drainage.

Arterial blood gases breathing air were taken on days 1 and 3 of the first week (pre and post control saline), and on days 7 and 9 (pre and post LTA-T) to identify any impaired gas exchange (which is a problem with talc pleurodesis). The efficiency of lung oxygen exchange was quantified from the change in the alveolar to arterial gradient for the partial pressure of oxygen calculated from these blood gas samples, using standard methods.

Patient symptoms, performance status, radiographic pleural fluid recurrence (chest radiograph), adverse events and the clinical need for further pleural fluid drainage was assessed on days 22, 43, 64, 85. Where further fluid drainage was required, the time from the administration of LTA-T to first drainage was recorded. Those with recurrent pleural fluid were offered sterile talc pleurodesis (as standard care). All patients were followed up to death.

Changes in continuous variables were compared to baseline using a paired t-test (SPSS version 12.0).

Results

Patient Characteristics

The characteristics of the 14 patients recruited are shown in table 1 along with dosing schedules.

TABLE 1

| Parameter | Results | |
|---|---|---|
| Age yrs (SD) | 57 (13) | |
| Sex | 6M: 8F | |
| Karnofsky performance index on recruitment | | |
| %(median, IQR) | 80 (60-90) | |
| Primary tumour site | Epithelioid Mesothelioma | 4 |
| | Adenocarcinoma Breast | 7 (3 ductal, 4 NOS) |
| | Ovarian Adenocarcinoma | 1 |
| | Adenocarcinoma, unknown primary | 1 |
| | Non-small Cell Lung Cancer | 1 (squamous) |
| Average Survival | | |
| Days median (IQR) | 108 (103-180) | |
| Blood parameters | | |
| mean (SD) | | |
| Hb (g/dL) | 13.1 SD 1.87 | |
| White Cell Count ($\times 10^6$) | 10.9 SD 8.4 | |
| Platelets ($\times 10^6$) | 394 SD 116 | |
| PT (secs) | 12.6 SD 2.0 | |
| APTT (secs) | 26.6 SD 5.7 | |
| Sodium (mmol/L) | 138 SD 2.4 | |
| Potassium (mmol/L) | 4.1 SD 0.4 | |
| Urea (mmol/L) | 6.2 SD 2.3 | |
| Creatinine (mmol/L) | 86 SD 17.0 | |
| Gamma GT (mmol/L) | 131.6 SD 261 | |
| Dose Escalation* | | |
| Pts 1 to 3 | 250 mcg | |
| Pts 4 to 6 | 375 mcg | |
| Pt 7, 9, 10 | 750 mcg | |
| Pts 11-13 | 1500 mcg | |
| Pt 14 | 3000 mcg | |

*= Patient 8 deteriorated due to rapidly progressive malignant disease, before the administration of any trial drugs. This patient's results are excluded from the analysis.

Dose Escalation and Toxicity

The initial dose, based on prior human and animal experience was a 250 mcg intrapleural. There were no adverse events after administration of intrapleural saline control. The second patient experienced mild fever (subsequently shown to be a concomitant urinary tract infection, table 2), and the dose escalation was halved for patients 3 & 4. Patient 8 deteriorated rapidly from progressive malignancy without receiving LTA-T and was withdrawn from the study. This patient's data is excluded from the analysis. The study was terminated when patient 14 (3,000 mcg), developed a systemic inflammatory reaction likely to be attributable to the trial drug, requiring hospital re-admission. The therapeutic dose was found to be 750 mcg to 1500 mcg based on the presence of detectable systemic inflammation at this dose identified from a rise in white blood cell count, FIG. 3b.

TABLE 2

Individual patient LTA-T doses and toxicity descriptions

| Patient Number | Dose (microgram's) | Dose per kg body weight (mcg/kg) | Side effects |
|---|---|---|---|
| 1 | 250 | 4.53 | Nil |
| 2 | 250 | 4.76 | Mild chest pain 2 hours post administration of LTA-T, lasting few hours. Twelve hours after administration, tachycardia, fever - settled with no specific treatment within 12 hours. Found to have a urinary tract infection (*E. coli* in urine culture) retrospectively |
| 4 | 375 | 5.17 | Nil |
| 5 | 375 | 5.23 | Nil |
| 6 | 375 | 6.13 | Mild headache and light headed 4 hours after LTA-T administration. Resolved spontaneously within 8 hours. Observations and examination normal |
| 7 | 750 | 10 | Nil |
| 8 | Withdrawn pre trial drug administration | Not Applicable | Not Applicable |
| 9 | 750 | 9.87 | Mild back pain on inspiration after LTA-T, resolved within 24 hours on no treatment |
| 10 | 750 | 12.10 | Nausea, vomiting and pyrexia for 3 days post LTA-T administration. Raised inflammatory markers (CRP > 285). Resolved spontaneously on no specific treatment. Patient known to have previous similar reactions to chemotherapy agents |
| 11 | 1500 | 29.07 | Nil |
| 12 | 1500 | 20.33 | Nil |
| 13 | 1500 | 22.42 | Nil |
| 14 | 3000 | 45.18 | Fevers, and vomiting associated with an inflammatory response and pain on side of LTA-T administration, within 24 hours. Required re-admission to hospital. |

Alveolar to Arterial Gradient in the Partial Pressure of Oxygen.

The change in the alveolar to arterial gradient for the partial pressure of oxygen was similar following LTA-T and saline control (LTA-T, mean baseline (SD) 4.24 (2.92) kPa, post LTA-T 4.88 (1.80) kPa, difference −0.64 (1.98) kPa, 95% C.I. diff −2.29 to 1.02, p=0.39; control saline, baseline 4.86 (2.00) kPa, post saline 4.69 (1.92) kPa, diff 0.17 (0.92) kPa, 95% C.I. difference −0.45 to 0.79, p=0.55, paired t-test).

Pleural Fluid Control

In one patient, advanced deposition of tumour on the visceral pleura entirely prevented lung expansion, and so fluid control through pleurodesis was not achievable.

In the other 13 subjects, the rate of pleural fluid production showed a strong trend towards reduction after LTA-T (total pleural fluid drainage during the 7 days before LTA-T (control saline week) mean 1597 SD 1541 mls, total drainage over 7 days after LTA-T 993 SD 1577 mls, dif. 603 SD 1006 mls, 95 C.I. −35 to 1242, p=0.062, paired t-test, FIG. 2 panel A).

In the 7 subjects receiving sufficient LTA-T (>750 mcg) to produce a systemic white cell count rise ('therapeutic dose'), the volume of pleural fluid drainage fell significantly (saline control week 1244 SD 933 mls, LTA-T week 394 SD 375 mls, dif. 850 SD 699 mls, 95 C.I. 204 to 1497, p=0.018, paired t-test, FIG. 2 panel B).

Long-term pleural fluid control was assessed by noting which patients required late therapeutic (>500 mls) pleural fluid drainage from their indwelling catheter in association with symptoms (excluding the subject not capable of achieving pleurodesis due to trapped lung). $^{12}/_{13}$ (92%) patients did not require any further therapeutic pleural drainage beyond 1 month from trial entry. Between day 14 (when the indwelling catheter was first locked closed) and 1 month, 3 further patients received one therapeutic fluid drainage (pleurodesis success from day 14 $^{9}/_{12}$ (75%)). In those patients receiving a dose >750 mcg of intrapleural LTA-T, $^{6}/_{7}$ required no therapeutic drainage at 1 month (86% pleurodesis success rate).

Peripheral Blood White Cell Count

Overall, there was a strong trend towards a higher peripheral blood white cell count (WCC) after LTA-T (WCC change after saline control mean 0.109 SD 0.80, change after LTA-T mean 2.81 SD 4.0, diff 2.72 SD 4.35, 95% C.I. 0.40 to 5.49, p=0.053, paired t-test, FIG. 3 panel A).

In the 7 subjects receiving >750 mcg LTA-T, there was a significant increase in WCC (change after saline 0.21 SD 0.38, change after LTA-T 4.49 SD 3.65, diff 4.70 (3.77), 95% C.I. 1.21 to 8.18, p=0.016, paired t-test, FIG. 3 panel B).

Thus, LTA-T was tested in 13 humans in a phase 1/2a clinical trial. In this trial a dose of 750 mcg to 1000 mcg produced effective pleurodesis, with almost no pain, no evidence of depressed blood oxygen levels and no other significant adverse effects.

This trial established a therapeutic dose of 750-1500 mcg (equating to 10-20 mcg/kg). Toxicity at the therapeutic dose was mild with no consistent side effect profile, and was substantially less than expected with the clinical standard of talc pleurodesis. No blood parameter, performance status or respiratory status toxicities were seen.

Intrapleural LTA-T administration was followed by a reduction in pleural fluid production over the week after drug administration. In addition, effective pleurodesis occurred in 75% of subjects after one month, where pleurodesis was technically achievable. This is comparable to the therapeutic efficacy of talc pleurodesis but without the side effects associated with talc pleurodesis.

The toxicity profile of LTA-T compares favourably with that of intra-pleural talc, the most commonly used pleurodesis agent in the UK, USA and worldwide.

The invention claimed is:

1. A method of treating pleural effusion or pneumothorax in a subject in need thereof comprising intrapleural administration of lipoteichoic acid T to the subject in a dosage of between 50 and 3000 micrograms.

2. The method of claim 1 wherein the subject is a mammal.

3. The method of claim 2 wherein the subject is a human.

4. The method according to claim 1, wherein the lipoteichoic acid T is administered in combination with a further pleurodesis agent.

5. The method according to claim 2, wherein the lipoteichoic acid T is administered in combination with a further pleurodesis agent.

6. The method according to claim 3, wherein the lipoteichoic acid T is administered in combination with a further pleurodesis agent.

7. The method according to claim 4, wherein the further pleurodesis agent is one or more agent selected from intrapleural talc, minocycline, Cornebacterium parvum, doxycycline, tetracycline, methylprednisolone acetate, fluorouracil, bleomycin, interferon-B, mitomycin-C, cisplatin, doxorubicin, transforming growth factor-beta (TGF-beta), quinacrine, 2% polydocanol, OK-432, Streptococcus pyogenes, fibrin tissue adhesive, povidone iodine, silver iodide, barium sulphate, plidocanol, etoposide and ipovidone.

8. The method according to claim 4, wherein the further pleurodesis agent is selected from peptidoglycan, atypical LPS (lipopolysaccharide), MALP-2 and MALP-404 (lipoproteins), OspA, porin, antigen mixtures, LcrV, lipomannan, qlycosylphosphatidylinositol (GPI anchor), lysophosphatidylserine, lipophosphoglycan (LPG), zymosan, heat shock protein 60 (hsp60) and hemagglutinin.

9. The method according to claim 1, wherein the lipoteichoic acid T is administered in the form of a pharmaceutical composition.

10. The method according to claim 1, wherein the lipoteichoic acid T is administered in the form of a solution or suspension.

11. The method according to claim 1, wherein the lipoteichoic acid T is administered in a dosage of between 250 micrograms and 3000 micrograms.

12. The method according to claim 1, wherein the lipoteichoic acid T is administered in a dosage of between 300 micrograms to 400 micrograms.

13. The method according to claim 1, wherein the lipoteichoic acid T is administered in a dosage of between 700 micrograms to 800 micrograms.

14. The method according to claim 1, wherein the lipoteichoic acid T is administered in a dosage of between 900 micrograms to 1100 micrograms.

15. The method according to claim 1, wherein the lipoteichoic acid T is administered in a dosage of between 1450 micrograms to 1550 micrograms.

16. The method according to claim 1, wherein the dosage is administered in an amount of between 10-20 micrograms/kilogram body weight.

17. The method according to claim 1, wherein the lipoteichoic acid T is administered in a dosage of between 50 micrograms to 550 micrograms.

18. The method according to claim 4, wherein the lipoteichoic acid T and the further pleurodesis agent are administered simultaneously, separately and/or sequentially.

19. The method of claim 1 wherein the subject is a sheep, cow, pig, chicken, goat, cat, dog, or horse.

20. The method according to claim 1, wherein the lipoteichoic acid T is administered after pneumothorax or pleural effusion has been resolved.

* * * * *